United States Patent
Davidov et al.

(10) Patent No.: US 6,780,011 B2
(45) Date of Patent: Aug. 24, 2004

(54) DENTAL ARTICULATOR WITH EXTENDED MOTION RANGE

(76) Inventors: Evgeny Davidov, 84-20 Austin St., Apt. 3F, Kew Gardens, NY (US) 11415; Vyacheslav Iskhakbayev, 83-60 118th St., Apt. 1B, Kew Gardens, NY (US) 11415

( * ) Notice: Subject to any disclaimer, the term of this patent is extended or adjusted under 35 U.S.C. 154(b) by 0 days.

(21) Appl. No.: 10/282,796

(22) Filed: Oct. 30, 2002

(65) Prior Publication Data

US 2003/0180683 A1 Sep. 25, 2003

Related U.S. Application Data

(63) Continuation-in-part of application No. 10/103,046, filed on Mar. 22, 2002, now Pat. No. 6,712,609.

(51) Int. Cl.$^7$ .............................................. A61C 11/00
(52) U.S. Cl. ........................................... 433/64; 433/63
(58) Field of Search .............................. 433/53, 54, 57, 433/60, 61, 62, 63, 64, 65, 66

(56) References Cited

U.S. PATENT DOCUMENTS

| | | | |
|---|---|---|---|
| 175,046 A | 3/1876 | Davidson | |
| 530,524 A | 12/1894 | Hitch | |
| 981,430 A | 1/1911 | Kennedy | |
| 1,381,794 A | * 6/1921 | Edgar | 433/58 |
| 2,200,058 A | * 5/1940 | Chott | 433/59 |
| D204,381 S | * 4/1966 | Orofino | D24/182 |
| 4,196,518 A | 4/1980 | Benzaria | |
| 4,265,619 A | 5/1981 | Lucki | |
| 4,319,875 A | 3/1982 | Beckwith | |
| 4,496,320 A | 1/1985 | Hwang | |
| 4,734,033 A | 3/1988 | Huffman | |
| 4,818,228 A | 4/1989 | Berceaux | |
| 4,854,868 A | 8/1989 | Pitre | |
| 5,007,829 A | * 4/1991 | Farrell | 433/61 |
| 5,106,296 A | 4/1992 | Varde | |
| 5,267,858 A | 12/1993 | Ono | |
| 5,506,095 A | 4/1996 | Callne | |
| 5,605,456 A | 2/1997 | Young | |
| 5,769,634 A | 6/1998 | Choi | |

FOREIGN PATENT DOCUMENTS

| | | |
|---|---|---|
| DE | 2923208 | 11/1980 |
| FR | 2590475 | 5/1987 |

* cited by examiner

Primary Examiner—Cary E. O'Connor
(74) Attorney, Agent, or Firm—I. Zborovsky

(57) ABSTRACT

The invention is a dental articulator with an extended range of motion of the maxilla relative to the mandible The articulator includes a base and a mandibular assembly extending horizontally from that base. A mandibular plate is provided with a supporting structure, which is aligned with corresponding cavities in the mandibular base cast for easy removal and attachment. A base is further equipped with a vertical post slidingly positioned on a vertical shaft of that base. A maxillary assembly is retained on that post via a ball-and-socket arrangement and further via a horizontal shaft positioned in two semi-opened sockets and retained by a spring-biased pin. The maxillary assembly contains a plate supporting a removable base cast in a manner similar to that of the mandibular assembly. The articulator saves time and allows for easy positioning of the maxilla and mandible.

7 Claims, 3 Drawing Sheets

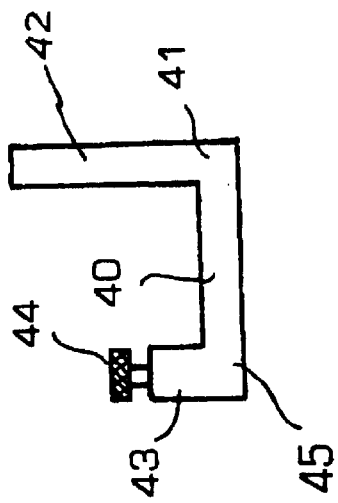
Fig. 11
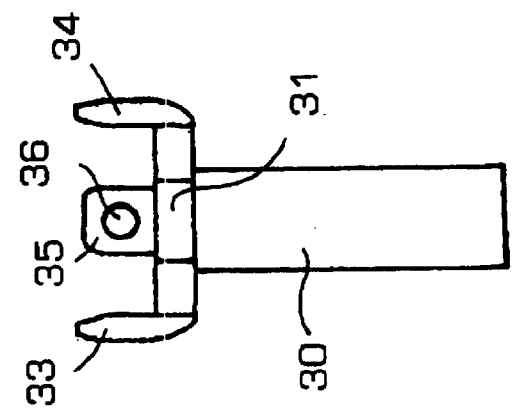
Fig. 12
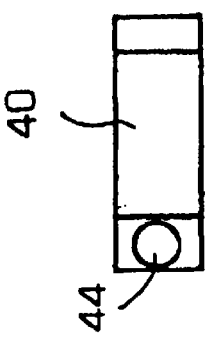
Fig. 9
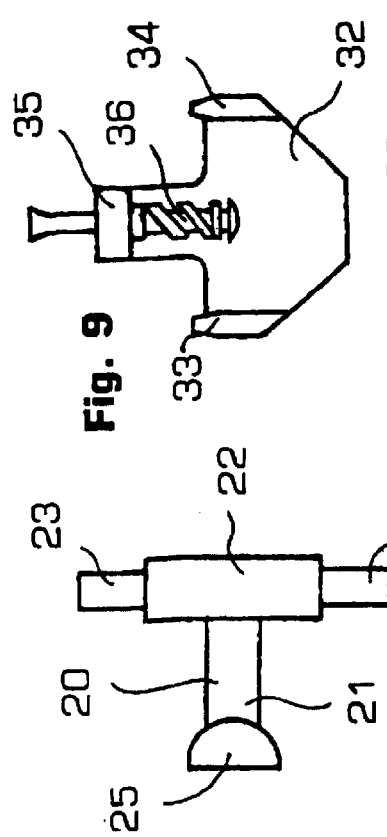
Fig. 10
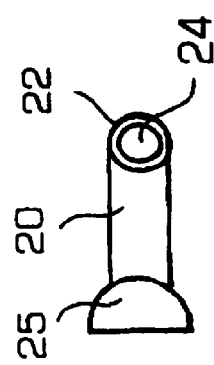
Fig. 7
Fig. 8

DENTAL ARTICULATOR WITH EXTENDED MOTION RANGE

CROSS-REFERENCE DATA

This is a continuation-in-part of a patent application Ser. No. 10/103,046 filed Mar. 22, 2002 entitled "Supporting Structure for a Dental Model and a Method for Forming Thereof", now U.S. Pat. No. 6,712,609, which is incorporated herein in its entirety.

FIELD OF THE INVENTION

The present invention generally relates to locking devices and more particularly to an improved locking device for a dental articulator with dental model casts.

BACKGROUND OF THE INVENTION

To accurately form and position false teeth or caps, a dentist normally makes a negative impression of the affected tooth or teeth. The negative impression may be partial, unilateral or bilateral, depending upon the extent of work to be done; the negative impression serves as a mold for developing a die of the patient's tooth or teeth. The negative impression is obtained by partially filling a tray with thermoplastic material. The filled tray is inserted within the patient's mouth such that the teeth and adjacent gum sink into and create a cavity within the thermoplastic material. Shortly thereafter, the thermoplastic material will cure and retain an exact impression of the patient's teeth and adjacent gum. This is an essentially standard technique to produce a dental cast presently used by most dentists.

Dental articulators for use with casts of a dental model to develop prosthetic dentures or denture elements have been used for a number of years. These articulators range from a very simple device affording only fixed pivotal movement between a pair of casts to highly sophisticated and mechanically complex devices which are capable of simulating the full range of occlusal and masticatory registration unique to any patient. The relatively simple devices are generally inadequate to provide sufficiently accurately registered prosthetic restoration to avoid extensive visits with a dentist to obtain adjustments thereof while the very complex devices are time consuming to operate and require extensive training to use properly. In either situation, the costs incurred to the patient are substantial. Moreover, none of the prior art articulators permit disengagement of the casts from registration with one another without extensive realignment upon reengagement. Thus, a technician is usually forced to perform his work while the casts are mounted on the articulator. Such an environment is difficult to work in with speed and accuracy. At the minimum, the vertical bite, any lateral or protrusive misalignments of the maxilla (upper jaw) and the mandible (lower jaw), and the inclinations of maxilla and mandible relative to an axis passing through the condyles when the mouth is closed have to be reproduced by a good articulator.

Each of the following listed U.S. patents are directed to dental articulators which incorporate lockable ball-and-socket elements to afford pivotal movement and extensible members to afford translational movement: U.S. Pat. Nos. 175,046; 530,524; 537,812; 565,326; 981,430; 1,736,006; 1,841,729; 2,571,280; 2,600,899; 2,608,762; 2,621,407; 2,765,533; 4,1,69,314; 4,196,518; and Belgian Pat. No. 572,850.

An articulator which provides structure to effect a simple hinged movement without provision of mechanical structure for defining translatory movement of multi-axis pivotal movement is disclosed in U.S. Pat. No. 2,430,177. Simulation of the full range of occlusal and masticatory registration is obtained by resiliently flexing the articulator. Such resiliency is afforded by the coil spring like configuration of a wire element defining each leg of two pairs of legs. For a well-trained and experienced technician, the freedom of movement afforded by this articulator is sufficient to permit the formation and adjustments of most prosthetic dentures. Accurate use of the device is predicated upon the formation of elongated sockets within each cast of a dental model for receiving, capturing and retaining each of the four wire legs. The casts usually vary in overall physical size, depending upon the size of the patient's teeth to be simulated and the size and configuration of the base formed. To employ the articulator described in this patent, uniformity of spacing during formation of the casts is time consuming and requires an experienced technician. No adjustment capability exists within the articulator itself to accommodate differences in spacing, as would be expected, as the size of a pair of casts vary in proportion to the physical size of the patient's jaws and the usually uniquely sized bases therefor. Other U.S. Patents describing articulators include U.S. Pat. Nos. 824,096, 3,429,045 and 3,466,750.

U.S. Pat. Nos. 4,734,033; 4,818,228; and 5,769,634 each illustrate more examples of a design for a dental articulator with a ball-and-socket joint. The limitation of these designs is that this joint is the only adjustable element allowing the upper dental cast to tilt around a horizontal axis extending through the center of the ball as well as about the vertical axis extending through the same ball. Extended range of motion is sometimes needed to accommodate a wider pool of patients. These articulators do not allow for that possibility.

It is also critical to check for any misalignment during the preparation of the dental prosthesis. In order to do so, a swinging motion is required from a dental articulator to simulate that of a human lower jaw. U.S. Pat. Nos. 4,496,320; 5,267,858; and 5,605,456 illustrate one particular element allowing for that motion. More specifically, a horizontal pin is supported by a spring and pivotally connects the upper cast to the base so that temporary dislodgment is possible to swing the upper cast to the left or to the right from the base itself. Such design allows to some approximation of the movements of the natural human jaw. However, these articulators do not afford the flexibility and range needed to accommodate most of the needs of dental patients.

The need exists therefore for a simple to use articulator which at the same time allows for a wide range of motions and accommodates an extended range of motion necessary for some dental patients.

SUMMARY OF THE INVENTION

It is an object of the present invention to provide a dental articulator with extended range of motion for maxillary and mandibular dental casts.

It is another object of the invention to provide a dental articulator allowing for quick removal and attachment of both maxillary and mandibular dental casts.

It is a further object of the invention to provide a dental articulator accurately simulating any lateral motion of the maxilla relative to the mandible.

It is yet another object of the invention to provide a dental articulator to reproduce any protrusive misalignments of the maxilla relative to the mandible.

In its preferred form, the dental articulator of the present invention has a base and a mandibular assembly extending from the front portion of the base. A vertical post extends from the rear portion of the base and pivotally supports a maxillary assembly.

The mandibular assembly comprises a mandibular plate supporting a removable mandibular base cast. The mandibular plate contains a rectangular (or otherwise non-circular) shaft extending through a corresponding opening in the front portion of the base so that the position of the mandibular assembly can be adjusted by sliding it in and out of the base. Once the desirable position is achieved, it is fixed in place by applying a set crew or other similar well-known fixation means.

The mandibular base cast of the dental articulator is provided with at least one cavity extending internally into the cast from its bottom surface. The shape of the cavity is determined by the mold forming the base cast. In one embodiment, the cavity has straight walls. In another embodiment (not shown on the drawings), the cavity is barrel-shaped. The mandibular plate is provided with an alignment structure, which includes a pair of straight-walled projections, for use in combination with the straight-walled cavity, or a pair of curved springs, for use in combination with barrel-shaped cavity. The mandibular plate is secured to the base cast by inserting and retaining the alignment structure inside the provided cavities.

The vertical post extends from the articulator base and contains a set screw so that its position can be fixed in space. The rear portion of the articulator base contains a rectangular vertical shaft adapted to be placed inside a corresponding opening in the vertical post next to a set screw. The vertical post can slide up and down that shaft for position adjustment.

The top portion of the vertical shaft contains two semi-open sockets positioned on the sides of the post and a spring-biased pin aimed at the middle between the sockets. A shaft of the maxillary support element is placed in the sockets and is retained there by the spring-biased pin. Such arrangement is by itself known in the prior art to allow for lateral motion of the maxillary assembly.

The maxillary support element contains a shaft in its rear portion for placement into the sockets of the vertical post. A separate socket is positioned in its front portion to form a ball-and-socket joint with the maxillary plate.

Maxillary assembly consists of a maxillary plate and a removable maxillary base cast. The plate contains a ball to be attached to the socket of the maxillary support element as well as the retaining structure to mate with the corresponding features of the maxillary base cast. The maxillary base cast is made in a similar manner to that of the mandibular base cast which allows for easy removal and attachment of the base cast to the corresponding plate.

The above and other objects, aspects, features and advantages of the invention will be more readily apparent from the description of the preferred embodiments thereof taken in conjunction with the accompanying drawings and appended claims.

BRIEF DESCRIPTION OF THE DRAWINGS

The invention is illustrated by way of example and not limitation and the figures of the accompanying drawings in which like references denote like or corresponding parts, and in which:

FIG. 7 is a top view of the maxillary support element;

FIG. 8 is a side view of the same;

FIG. 9 is a top view of the vertical post of the articulator;

FIG. 10 is a front view of the same;

FIG. 11 is a top view of the base of the articulator; and finally

FIG. 12 is a side view of the same.

DETAILED DESCRIPTION OF THE PREFERRED EMBODIMENT AND THE DRAWINGS

Figure 2:
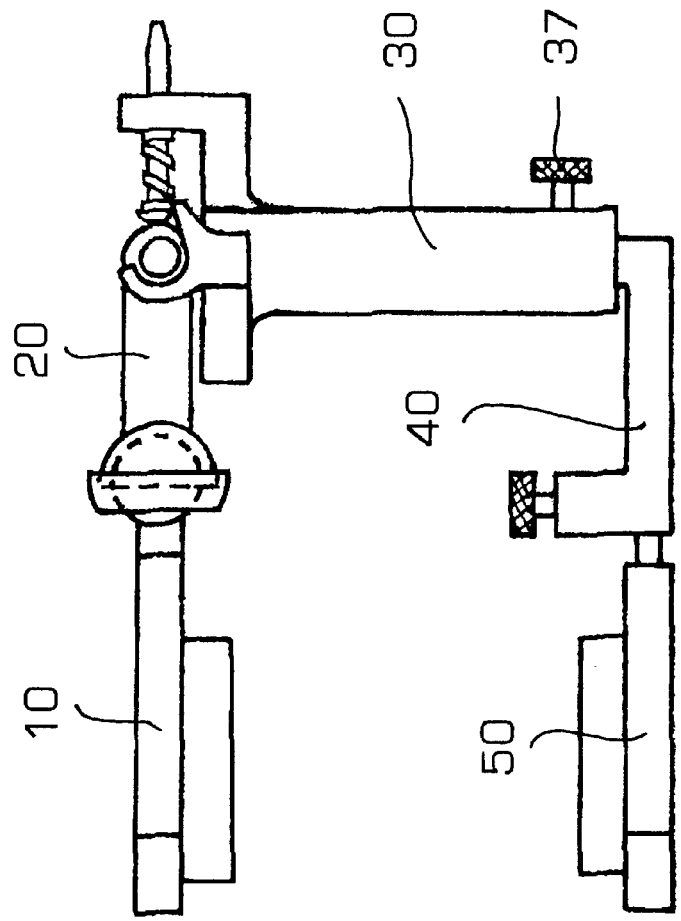
FIG. 2 is a general side view of the same dental articulator.
Figure 1:
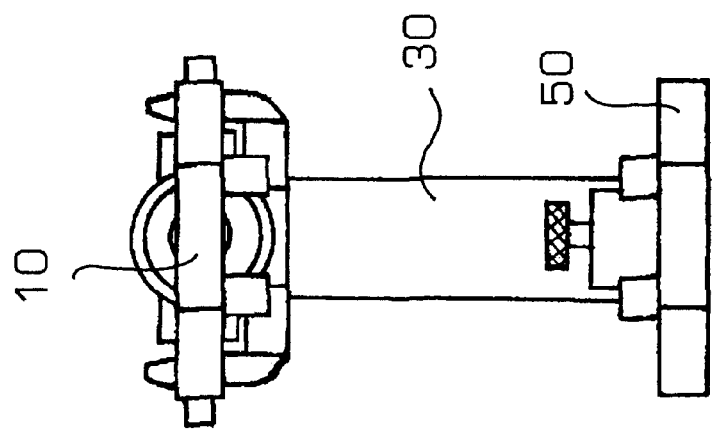
FIG. 1 is a general front view of the dental articulator of the present invention.
Figure 3:
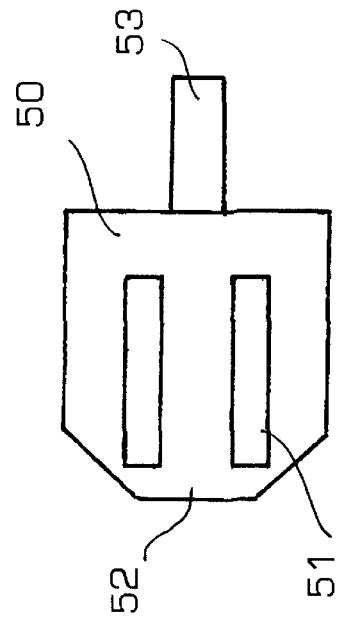
FIG. 3 is a bottom view of the maxillary plate of the articulator.
Figure 4:
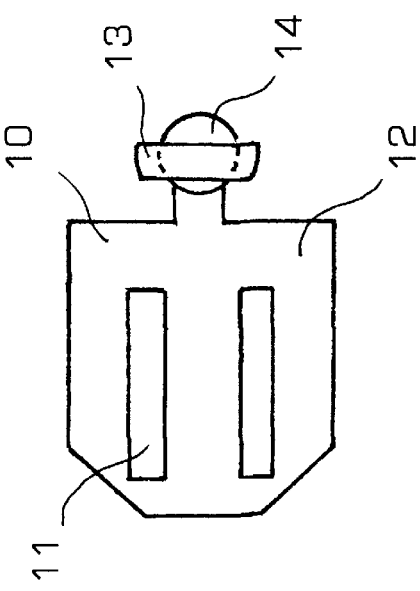
FIG. 4 is a side view of the same as in FIG. 3.

Referring to FIGS. 1 and 2, there is shown a dental articulator according to the present invention to include a base 40 and a mandibular assembly 50 extending from the front portion of the base 40. A vertical post 30 extends from the rear portion of the base 40 and pivotally supports a maxillary assembly 10 via a maxillary support element 20.

The base 40 is shown in detail on the FIGS. 11 and 12 and includes a front portion 45 and a rear portion 41. An horizontal retaining means 43 is extended from the front portion 45 of the base 40 and includes an opening to accept the shaft of the mandibular assembly (not shown) and the set screw 44 to fix the position of the mandibular assembly once it is appropriately adjusted. The rear portion 41 of the base 40 contains a vertical shaft 42 of a rectangular or any other appropriate non-circular shape in cross-section to accept a corresponding opening in the vertical post 30.

Figure 5:
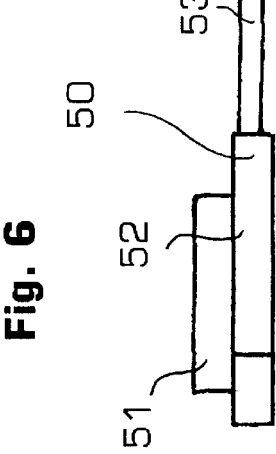
FIG. 5 is a top view of the mandibular plate of the articulator.
Figure 6:
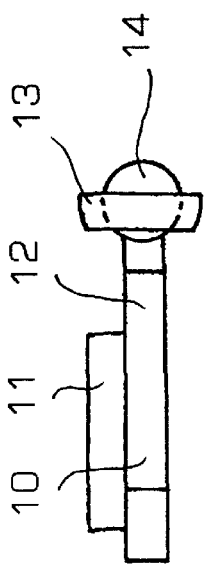
FIG. 6 is a side view of the mandibular plate.

The mandibular assembly 50 is illustrated on FIGS. 5 and 6 and comprises a mandibular plate 52 supporting a removable mandibular base cast (not shown). The mandibular plate 52 contains a rectangular (or otherwise non-circular) shaft 53 extending through a corresponding opening in the front portion 45 of the base 40 so that the position of the mandibular assembly 50 can be adjusted by sliding it in and out of the base 40. Once the desirable position is achieved, it is fixed in place by tightening the set screw 44. This arrangement allows compensating for any protrusive misalignments of the lower jaw of the patient.

Since the mandibular base cast of the dental articulator is provided with at least one internal cavity, the mandibular plate 52 is provided with an alignment structure 51. This structure is a pair of straight-walled projections, for use in combination with the straight-walled cavity. The mandibular base cast can be removably secured to the plate 52 by inserting and retaining the alignment structure inside the provided cavities in the base cast. Other geometrical shapes of retaining structure are possible of course and would be apparent for those skilled in the art.

The vertical post 30 extends from the articulator base 40 and is shown in detail on FIGS. 9 and 10. It contains a set screw 37 on the bottom and an opening (not shown) to accept the vertical shaft 42 of the base 40 forming a vertical retaining means together with the set crew 37. The vertical post 30 can therefore slide up and down the shaft 42 for position adjustment.

The top portion 31 of the vertical post 30 contains two semi-open sockets 33 and 34 positioned to the sides of the top plate 32 and a spring-biased pin 36 aimed at the middle between the sockets 33 and 34. The pin 36 is placed in the rear offset base 35 of the plate 32. The sockets 33 and 34 are adapted to accept the maxillary support element 20 shown in detail on FIGS. 7 and 8. It contains a shaft 22 with extended ends 23 and 24 to be placed in the openings of the sockets 33 and 34 respectively. A spring-biased pin 36 supports the shaft 22 in the middle when it is placed inside the sockets 33 and 34. Such arrangement is by itself known in the prior art to allow for lateral motion of the maxillary assembly as the extended ends 23 or 24 are moved out of their respective socket positions but the whole assembly is still retained together by a pin 36. This design allows for lateral swings of the maxillary assembly to simulate the lateral swings of the patient's maxilla.

The maxillary support element 20 also contains a support base 21 to which the above mentioned shaft 22 is attached in a perpendicular orientation. A separate socket 25 is positioned in its front portion of the element 20 to form a ball-and-socket joint with the maxillary assembly 10.

Maxillary assembly 10 in turn consists of a maxillary plate 12 and a removable maxillary base cast (not shown). The plate 12 contains a ball 14 to be attached to the socket 25 of the maxillary support element 20 via a nut 13 or any other similar tightening means. The retaining structure 11 is also provided on the plate 12 to mate with the corresponding features of the maxillary base cast, similarly to that of the mandibular base cast.

The dental articulator of the present invention has an advantage of allowing for faster assembly of the maxilla and mandible models. After casting the upper and lower bases, they are simply removed from the molds, attached to the corresponding plates of the articulator and then aligned in position by loosening first of all set screws, positioning the jaw models and then tightening all crews again. This simple process can be easily adjusted without loosening the screws if needed since both maxillary and mandibular base casts are removable from their corresponding supporting plates. The need for a customary casting and then shaping of the dental models is therefore eliminated.

Another advantage of the present articulator is in a quite frequent situation when the original cast of the jaw relative positions is made with some inaccuracy. Typically, a new gypsum cast is needed to correct this situation. With the present invention, simple realignment of the jaw positions can be done by loosening and then re-tightening of one or several set screws as appropriate so that new casting is avoided.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

What is claimed is:

1. A dental articulator comprising:

a base equipped with horizontal retaining means and a vertical shaft, a mandibular assembly slidingly attached to said horizontal retaining means, said assembly including a mandibular plate and a mandibular base cast removably attached thereto, a vertical post equipped with a vertical retaining means, said post slidingly attached to said base by positioning said vertical shaft inside said vertical retaining means, said vertical post further including a top plate, two semi-opened sockets placed on the sides of said plate and a spring-biased pin placed pointing to the center of said plate, a maxillary support element including a shaft, a support base, and a socket, said maxillary support element hingedly attached to said vertical post by placing said shall into said semi-opened sockets and retaining thereof in place by said spring-biased pin, and a maxillary assembly equipped with a ball and a securing means, said ball adapted to be placed in said socket of said support element for form a ball-and-socket joint together with said securing means, said assembly further including a maxillary plate and a maxillary base cast removably attached thereto.

2. The dental articulator as in claim 1, wherein said maxillary and said mandibular plates having correspondingly bottom and top surfaces, said maxillary and said mandibular base casts made from a single non-deformable material and having corresponding top and bottom surfaces in opposing relationship to said bottom and top surfaces of said maxillary and mandibular plates, said base casts each further comprising at least one elongated internal cavity vertically extending therein, said plates further comprising each at least one alignment means, said alignment means having an outer shape substantially conforming to an inner shape of said cavities.

3. The dental articulator as in claim 1, wherein said horizontal and said vertical retaining means each including a set screw.

4. The dental articulator as in claim 1, wherein said vertical shaft has a non-circular cross-sectional shape.

5. The dental articulator as in claim 4, wherein said vertical shaft has a rectangular cross-sectional shape.

6. The dental articulator as in claim 1, wherein said securing means is a retaining nut.

7. A dental articulator comprising:

a base equipped with horizontal retaining means and a vertical shaft, a mandibular assembly slidingly attached to said horizontal retaining means, said assembly including a mandibular plate and a mandibular base cast removably attached thereto, said mandibular plate having a top surface, said mandibular base cast made from a single non-deformable material, said mandibular base cast having a bottom surface in opposing relationship to said top surface of said mandibular plate and including an elongated cavity vertically extending therein, said mandibular plate further comprising an alignment means having an outer shape substantially conforming to an inner shape of said elongated cavity of said mandibular plate and adapted to attach said mandibular base cast with said mandibular plate with frictional immobility, a vertical post equipped with a vertical retaining means, said post slidingly attached to said base by positioning said vertical shaft inside said vertical retaining means, said vertical post further including a top plate, two semi-opened sockets placed on the sides of said plate and a spring-biased pin placed pointing to the center of said plate, a maxillary support element including a shaft, a support base, and a socket, said maxillary support element hingedly attached to said vertical post by placing said shaft into said semi-opened sockets and retaining thereof in place by said spring-bised pin, and a maxillary assembly equipped with a ball and a securing means, said ball adapted to be placed in said socket of said support element for form a ball-and-socket joint together with said securing means, said assembly further including a maxillary plate and a maxillary base cast removably attached thereto, wherein said maxillary plate having a bottom surface, said maxillary base cast made from a single non-deformable material, said maxillary base cast having a top surface in opposing relationship to said bottom surface of said maxillary plate and including an elongated cavity vertically extending therein, said maxillary plate further comprising an alignment means having an outer shape substantially conforming to an inner shape of said elongated cavity of said maxillary plate and adapted to attach said maxillary base cast with said maxillary plate with frictional immobility.

* * * * *